United States Patent [19]

Cassou et al.

[11] Patent Number: 4,701,164

[45] Date of Patent: Oct. 20, 1987

[54] GYNECOLOGICAL INSTRUMENTS, ESPECIALLY FOR TRANSFERRING EMBRYOS

[76] Inventors: Robert Cassou; Maurice Cassou, both of Rue Clémenceau; Bertrand Cassou, Saint Symphorien des Bruyeres, all of 61300 L'Aigle, France

[21] Appl. No.: 881,914

[22] Filed: Jul. 3, 1986

Related U.S. Application Data

[63] Continuation of Ser. No. 681,551, Dec. 14, 1984.

[30] Foreign Application Priority Data

Dec. 16, 1983 [FR] France ................................ 83 20172

[51] Int. Cl.[4] ................................................ A61M 1/00

[52] U.S. Cl. ...................................... 604/218; 604/60; 604/275

[58] Field of Search ...................... 604/218, 55, 57, 59, 604/60, 170, 236, 238, 264, 271, 270, 902, 217, 220, 285

[56] References Cited

U.S. PATENT DOCUMENTS

| | | | |
|---|---|---|---|
| 602,010 | 4/1898 | Hoenig | 604/217 |
| 740,910 | 10/1903 | Peloubet | 604/285 |
| 1,253,955 | 1/1918 | Galligan | 604/60 |
| 3,547,126 | 12/1970 | Birtwell | 604/102 |
| 4,173,227 | 11/1979 | Cassou et al. | 604/275 |
| 4,468,217 | 8/1984 | Kuzmick et al. | 604/902 |

FOREIGN PATENT DOCUMENTS

| | | | |
|---|---|---|---|
| 3233404 | 3/1984 | Fed. Rep. of Germany | 604/271 |
| 2070437 | 9/1981 | United Kingdom | 604/55 |

*Primary Examiner*—Stephen C. Pellegrino

*Attorney, Agent, or Firm*—Bachman & LaPointe

[57] ABSTRACT

This instrument is of the type comprising a hollow body housing a reservoir tube for reproductive components, 4, which receives an ejection piston rod and which is closely enveloped by an external protective sheath 7 having, at its distal end *7b*, retaining means 9 inside which the projecting end of the reservoir tube bears.

The problem to be solved consists in making it possible to avoid causing any lesions and carrying along any mucus and also to construct instruments of very small diameter.

According to the invention, the retaining means 9 on the sheath 7 comprises a terminal 9 with a solid rounded head or distal end 9*b* and with a blind axial passage 10 open towards the cylindrical body 1 and communicating with the outside at its blind end by means of a lateral transfer orifice 10*c*.

The invention has an advantageous application in the transfer of animal embryos.

11 Claims, 2 Drawing Figures

GYNECOLOGICAL INSTRUMENTS, ESPECIALLY FOR TRANSFERRING EMBRYOS

This is a continuation of Application Ser. No. 681,551 filed Dec. 14, 1984.

The present invention relates to gynecological instruments for humans and animals, which are intended more particularly for transferring reproductive components, i.e. placing them in the genital tract of the female, especially for artificial insemination or embryo transfer, the said instruments being of the type comprising a hollow, rigid cylindrical body inside whose distal end there is a housing of larger diameter for accommodating a reservoir tube for reproductive components, partially projecting beyond this end, a rigid axial piston rod mounted so as to slide in this cylindrical body and projecting beyond its proximal end, and an external protective sheath which closely envelops, also in a sliding fashion, the cylindrical body and the projecting end of the reservoir tube, this projecting end bearing on the inside of retaining means provided on the said sheath at its distal end.

Instruments of this type are already known, in their two main uses mentioned above, for example from French Pat. No. 1,467,943 in the name of the first of the present three Applicants, in the context of artificial insemination, and from French Pat. No. 80/04,607 (publication No. 2,477,066) in the names of these same three Applicants, in the context of embryo transfer. In both cases, the said retaining means provided on the end of the protective sheath consist of a frustoconical bearing surface presented internally by a terminal or lining fitting into the end part of this sheath, the said terminal offering, beyond this frustoconical bearing surface, an axial evacuation passage which emerges at the end of the terminal.

However, in the case of embryo transfer and also in the case of artificial insemination, it is difficult, with such an arrangement, for the end of the instrument covered with its sheath to penetrate deeply without causing lesions or hematomas, the risk being all the greater if the orifice of the axial passage encounters folds in the mucous membrane of the vaginal tract. Furthermore, during insertion of the instrument, this same orifice has the serious disadvantage of carrying along the vaginal mucus present along its path, so that once this mucus has been carried into the uterus, in the case of embryo transfer, it presents a serious risk of causing a total absence of implantation. Finally, the same structure of terminal with an axial passage does not make it possible to reduce the overall size of the instrument and hence to pass through very narrow cervices uteri such as those of goats, sheep, vertebrate amphibians and dogs.

It is for this reason that the object of the present invention is to provide an instrument of the abovementioned type which makes it possible firstly to avoid causing any lesions and carrying along any mucus and secondly to construct systems of very small diameter.

For this purpose, the invention relates to an instrument of the abovementioned type wherein the said retaining means on the sheath comprise a terminal with a solid rounded head or distal end and with a blind axial passage open towards the cylindrical body and communicating with the outside at its blind end by means of a lateral transfer orifice.

By virtue of this arrangement, the rounded shape of the head of the terminal avoids causing any lesions and also prevents any possible immobilization by a fold in the mucous membrane, while the lateral location of the transfer orifice opposes the carrying along of any mucus. Finally, this structure permits a very considerable reduction in the diameter of the instrument, including its protective sheath, compared with the embodiments known hitherto, for example a reduction from a customary diameter of 4.6 mm to a diameter of 3 mm, so that the instrument has come to look like a "very narrow needle ending in a ball-point"; thus, although the sheath is rather inflexible because it is supported by the stainless steel of which the cylindrical body is generally made, the user can "play" with the flexibility of this "ball-point needle" in order to negotiate the movement of its end through the genital tract and more particularly through the winding bends in the cervix, which are very wavy in the case of species such as goats, sheep etc.

Particularly advantageously, the terminal can have, at the back of its rounded head, a cylindrical external surface possessing a shoulder whose height corresponds approximately to the thickness of the protective sheath which fits onto the cylindrical part of reduced diameter, located behind the said shoulder.

Preferably, the rounded head can have the shape of a portion of a sphere whose angle at the center is greater than 180°, this head opening the passage, as it were, to the rest of the instrument, which is of smaller diameter, thus making it even easier to introduce.

Advantageously, provision can be made for the terminal of the reservoir tube to possess two diametrically opposite, lateral transfer orifices both emerging in the blind axial passage. By virtue of this arrangement, the explusion of the reproductive component, namely embryo or sperm, is facilitated to the extent that, if the first lateral orifice becomes blocked through bearing against the mucous membrane or becomes filled with mucus, the component can be ejected without difficulty through the opposite orifice.

In a particular embodiment, the blind axial passage in the terminal can have a cylindrical part which is longer than the lateral orifice or orifices but of the same width, and to which a frustoconical part is connected, the said frustoconical part having a small angle at the vertex and diverging towards the cylindrical body; this arrangement permits optimum support for the distal end of the reservoir tube while at the same time even making it possible, if the dimensions are calculated with this in mind, for the diameter of the cylindrical part of the blind passage to be equal to the internal diameter of the tube and, consequently, for the reproductive component not to encounter an obstacle when it is ejected by the piston rod from the tube towards the passage, this being particularly important in the case of embryos, which are extremely delicate.

Further characteristics and advantages of the invention will become apparent from the following description, which is given by way of non-limiting examples and with reference to the attached drawings; in these drawings.

Figure 1:
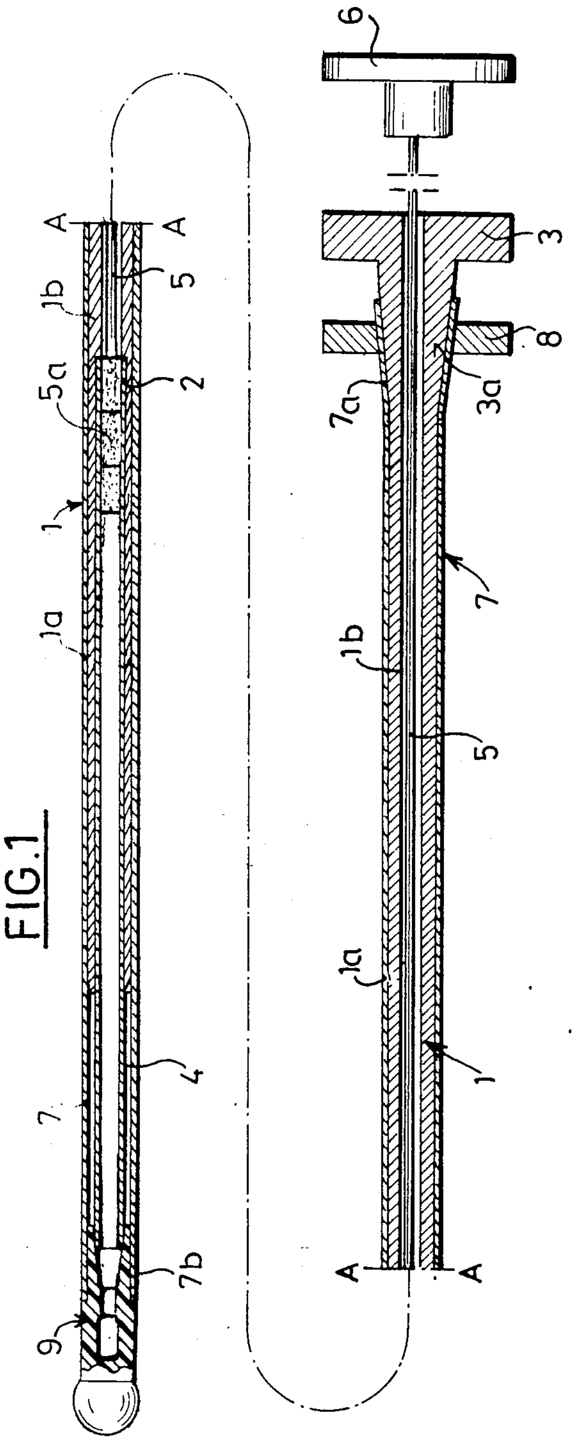
FIG. 1 shows a view of a gynecological instrument according to the invention, this view being in two parts which are separate for space reasons but are to be juxtaposed along the line A—A.

As shown in FIG. 1, the instrument illustrated is an instrument for transferring embryos, which comprises firstly a hollow, rigid cylindrical body 1, for example made of stainless steel, which is formed by the fitting of two metal tubes 1*a* and 1*b* into one another, the inner tube 1*b* being shorter than the other so that, at its proximal end, i.e. the end nearer the user, it is flush with the tube 1*a*, while at its distal end, it forms a shoulder 2 located at a distance from the distal end of the tube 1*a*. At their proximal ends, these two tubes are together surrounded by a third part 3 forming a supporting grip. The shoulder 2 delimits a housing 1*b*–2.

By virtue of the shoulder 2, this body thus forms a housing which can accommodate a cylindrical reservoir tube 4, called a "straw", which holds a suspension containing one or more embryos to be inserted. This reservoir tube 4 has approximately the same external diameter as the tube 1*b*, so that, by its proximal end, it bears in abutment against the shoulder 2 on the tube 1*b*, while its distal end partially projects, for example by ⅓ of its length, beyond the distal end of the tube 1*a*.

Furthermore, a rigid, solid axial piston rod 5, also made of stainless steel, is provided, the dialmeter of which enables it to be mounted so as to slide inside the tube 1*b* of the body, this piston rod having, at its proximal end, a gripping head 6 which remains outside the body 1 and near the head 3 of the latter when this rod 5 is fitted in the body. The length of the piston rod is such that its distal end acts, via a stopper 5*a* provided for this purpose inside the reservoir tube 4, to push back the whole of the contents of the latter towards its free distal end, i.e. its end which does not have a stopper or plug or, more precisely, which had a stopper on filling, the said stopper having been removed by cutting of the end section of the enveloping tube just before this tube was placed in the instrument. The rod 5 is made sufficiently long to permit complete ejection of the contents of the tube when the two heads 6 and 3 come into contact with one another.

The system is completed with an external protective sheath made of a semi-rigid plastic such as semi-rigid polyvinyl chloride, this sheath 7 having, in the same way as the rod 5, approximately the same length as the body 1 and being cylindrical over its entire length. Its internal diameter enables it closely to envelop the body 1 and to fit it, while its proximal end 7*a* is firmly held, after axial notching, to a frustoconical part 3*a* provided for this purpose on the head 3, for example by means of a locking ring 8. At its opposite distal end 7*b*, the sheath 7 is provided with an internal terminal 9, which will be described in detail and which is intended to form retaining means on this sheath for supporting the reservoir tube 4.

Figure 2:
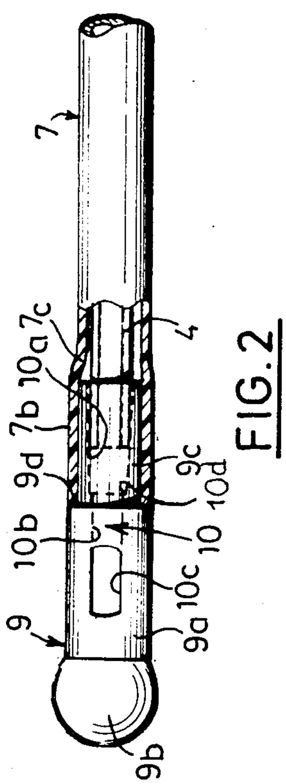
FIG. 2 shows a detailed view of the distal end of this instrument, i.e. the end opposite the user, on a larger scale.

As shown in greater detail in FIG. 2, this terminal 9 is formed by an element made entirely of plastic, for example flexible polyvinyl chloride. This terminal 9 has a central section with a cylindrical external surface 9*a*, the diameter of which is very precisely equal to the external diameter of the sheath 7, and it is extended forwards (distal end) by a rounded head formed of a solid portion of a sphere of larger diameter, 9*b*, with an angle at the center of the order of 250°, while at its proximal end it has a section of smaller diameter, 9*c*, which is connected thereto by a shoulder 9*d*, the height of which corresponds approximately to the thickness of the sheath 7. In this part of smaller diameter, 9*c*, is the first part 10*a* of a blind axial passage 10 open towards the cyindrical body 1, this part 10*a* having a frustoconical shape with a small angle at the vertex, for example 20°, and diverging towards the body 1; this part 10*a* is extended by a second, exactly cylindrical part of the passage, 10*b*, which runs over the greater part of the central section 9*a* of the terminal, the two parts being joined along a shoulder 10*d*. As from this end part 10*b* of the passage, and for example over approximately half its length, there are two lateral orifices or apertures 10*c*, diametrically opposite one another and of approximately rectangular cross-section, which emerge at the bottom of the passage 10 and whose width, transversely relative to the axis of the terminal, corresponds to the diameter or width of the part 10*b* of the passage, while these orifices are longer in the direction of the axis.

The distal end 7*b* of the sheath 7 fits over the part of smaller diameter, 9*c*, of the terminal with a slight expansion effect, which results in a restriction 7*c* connecting to the normal diameter of the sheath, and this fit extends to the level of the shoulder 9*d*.

What is claimed is:

1. A gynecological instrument comprising:
   - a hollow, rigid cyindrical body having a central bore of a first diameter with a distal end and a proximal end;
   - a housing carried by said distal end having a diameter larger than said first diameter;
   - a reservoir tube in said housing for reproductive components having an end part projecting beyond the distal end of the cylindrical body;
   - a rigid, axial piston rod mounted so as to slide in the cylindrical body and projecting beyond the proximal end thereof for sliding into the reservoir tube when said reservoir tube is accommodated in the cylindrical body;
   - an external protective sheath having a distal end, said sheath closely enveloping in a sliding fashion the cylindrical body and further enveloping the projecting end of the reservoir tube;
   - a terminal tip provided on said sheath at the sheath distal end wherein the projecting end of the reservoir tube bears on the inside of the terminal tip, the said terminal tip having an exteriorly rounded, solid head and behind said head two portions having different diameters separated by a shoulder, with a first portion of larger diameter than the second portion located at the back of said rounded head and having a cylindrical external surface wherein said shoulder has a height corresponding approximately to the thickness of the protective sheath, with said second portion comprising a cylindrical part of smaller diameter than the first portion located at the back of said first portion behind said shoulder, wherein the external protective sheath fits on said second portion as far as the shoulder, and wherein said rounded head of the terminal tip has the shape of a portion of a sphere with the diameter of the cylindrical external surface of said first portion being smaller than the largest diameter of the portion of a sphere;
   - an axial passage provided on the inside of said terminal tip, wherein the axial passage is blind at one of its ends and open towards the cylindrical body; and
   - a lateral transfer orifice of said terminal tip behind said rounded head providing communication for said terminal tip with the outside towards its blind end.

2. The instrument of claim 1 wherein the portion of a sphere has an angle at the center greater than 180°.

3. The instrument of claim 1 wherein the terminal tip possesses two diametrically opposite, lateral transfer orifices both emerging in the blind axial passage.

4. The instrument of claim 1 wherein the blind axial passage in the terminal tip has a cylindrical part with a proximal end, said cylindrical part being longer than the lateral orifice but of the same width, and to the proximal end of which a frustoconical part is connected, the said frustoconical part having a small angle at the vertex and divering towards the cylindrical body.

5. The instrument of claim 4 wherein the frustoconical part is connected to the cylindrical part by a shoulder.

6. The instrument of claim 1 wherein the cylindrical external surface of the terminal tip is located behind the shoulder and onto which the protective sheath fits, the diameter of the cylindrical external surface is slightly greater than the internal diameter of the protective sheath, and wherein the protective sheath is made of a sufficiently elastic material to allow the said fit.

7. The instrument of claim 1 wherein the terminal tip is made of flexible polyvinyl chloride.

8. The instrument of claim 1 wherein the protective sheath is made of semi-rigid polyvinyl chloride.

9. The instrument of claim 1 wherein the rounded head has the shape of a portion of a sphere.

10. The instrument of claim 1 wherein the portion of a sphere has an angle at the center greater than 180°.

11. The instrument of claim 1 wherein said lateral transfer orifice is located in the first portion of larger diameter.

* * * * *